United States Patent [19]

Freeman

[11] 3,949,750

[45] Apr. 13, 1976

[54] PUNCTUM PLUG AND METHOD FOR TREATING KERATOCONJUNCTIVITIS SICCA (DRY EYE) AND OTHER OPHTHALMIC ALIMENTS USING SAME

[76] Inventor: Jerre M. Freeman, 1509 Peabody Ave., Memphis, Tenn. 38104

[22] Filed: Oct. 7, 1974

[21] Appl. No.: 512,430

[52] U.S. Cl................. 128/260; 128/271; 128/1 R; 128/130; 128/341
[51] Int. Cl.² ................. A61M 29/00; A61M 31/00
[58] Field of Search .......... 128/260, 131, 130, 271, 128/341, 1 R, 350 R, DIG. 25

[56] References Cited
UNITED STATES PATENTS

| | | | |
|---|---|---|---|
| 1,042,624 | 10/1912 | Wagoner | 128/341 X |
| 2,592,800 | 4/1952 | Gariepy | 128/261 |
| 3,126,887 | 3/1964 | Gordon | 128/271 |
| 3,441,018 | 4/1969 | Schneider | 128/131 X |
| 3,626,940 | 12/1971 | Zaffaroni | 128/260 |
| 3,648,683 | 3/1972 | Brodie | 128/1 R |
| 3,699,951 | 10/1972 | Zaffaroni | 128/130 |
| 3,726,284 | 4/1973 | Parker | 128/350 R |
| 3,777,755 | 12/1973 | Groves | 128/285 X |
| 3,858,571 | 1/1975 | Rudolph | 128/1 R |

OTHER PUBLICATIONS

American Journal of Ophthamology, Vol. 73, May 1972, pp. 658, 659, "Lacrimal Function".

*Primary Examiner*—Aldrich F. Medbery
*Attorney, Agent, or Firm*—Chernoff & Vilhauer

[57] ABSTRACT

A plug of suitable dimension and material is removably inserted into the upper and/or lower punctal apertures of the eye to block the opening and the attendant canaliculus so as to thereby prevent the drainage of lacrimal fluid therethrough. The plug is comprised of tissue-tolerable, readily sterilizable material, such as polytetrafluorethylene (Teflon), or hydroxyethylmethacrylate (HEMA) hydrophilic polymer, methyl methacrylate, silicon, stainless steel or other inert metal material. The rod-like plug is formed with an oversized tip or barb portion that dilates and blockingly projects into the canaliculus, a smaller neck or waist portion upon which the punctum sphincter ring tightens, and a relatively larger, smooth head portion which rests upon the top of the punctal opening and prevents the plug from passing down into the canaliculus. In some embodiments the plug is impregnated with or otherwise acts as a carrier vehicle for an ophthalmic medication which is stored and delivered on a sustained release basis to the eye. A method for inserting the plug into the punctal opening is described, utilizing a dilator tool for enlarging the punctum and associated canaliculus and an inserter tool for facilitating the grasping, manipulation and insertion of the plug. The punctal plug has been found useful in treating keratoconjunctivitis sicca (dry eye) and is believed to be suitable for treating other ophthalmic ailments where retention of lacrimal fluid on the surface of the eye and in the lacrimal lake is desired or where sustained release of an ophthalmic medication to the eye by using the plug as a medication carrier is desired.

10 Claims, 8 Drawing Figures

PUNCTUM PLUG AND METHOD FOR TREATING KERATOCONJUNCTIVITIS SICCA (DRY EYE) AND OTHER OPHTHALMIC ALIMENTS USING SAME

BACKGROUND OF THE INVENTION

This invention relates to a punctum plug for removably closing the punctal openings of the eye and a method for treating keratoconjunctivitis sicca and other ophthalmic ailments using the plug as a means for preventing drainage of the lacrimal fluid from the eye or as a carrier vehicle for storing and delivering medication to the eye.

Keratitis sicca or keratoconjunctivitis sicca (referred to in layman's terms as dry eye), due to insufficient production or excessive drainage of lacrimal fluid, is a frequently-encountered ophthalmic problem, especially in elderly patients. Conventional prior art practice in treating such condition has been to utilize various types of topical drops and ointments with varying degrees of success. Humidifiers or vaporizers have also been used and are often of great help in decreasing evaporation from the dry eye, but do nothing to limit the drainage of the lacrimal fluid. In extreme cases of discomfort and pain, such as occurs in Sjogren's syndrome, permanent closure of the punctae and canaliculae by surgery or cauterization has produced marked success. However, each of the aforementioned treatments possess certain inherent limitations, the ointments by reason of the need for frequent and continued applications, and the surgical or cauterization procedure by reason of cost, danger of infection and irreversibility.

A paper by Lester T. Jones et al entitled "Lacrimal Function," appearing in *American Journal of Ophthalmology*, vol. 73, May 1972, pp. 658–659, described some brief experiments on student nurses using a tapered awl-like cone or tube of polyethylene material to temporarily occlude, for very short periods of time, either the upper or lower punctum and canaliculus while measurements were taken of the relative speed of lacrimal excretion through the unblocked other canaliculus. However, no effort has hithertofore been directed to utilizing a removable punctum plug as a means for treating keratoconjunctivitis sicca or other ophthalmic ailments or to designing a plug of suitable configuration for ready insertion, snug fitting without danger of ejection from the punctum or passage down into the canaliculus, and ready removal from the punctal opening. Nor has consideration been given to forming such a punctum plug from materials which would be readily sterilizable and non-irritating to the ophthalmic tissue structure over long-term wearing periods, and possessing sufficient tensile strength to resist breakage. Finally there has been no discussion in the prior art of utilizing a punctum plug as a vehicle or carrier means for storing and delivering topical medications to the eye over sustained periods of time.

SUMMARY OF THE PRESENT INVENTION

The present invention is directed to a plug for removably blocking the punctal opening and associated canaliculus for preventing the drainage of lacrimal fluid from the eye and/or for delivering topical ophthalmic medications thereto. The plug, which can be utilized to close the upper as well as the lower punctal opening although the latter is usually preferred, is comprised of three portions: (1) a projecting tip or barb portion which dilates and blockingly protrudes into the vertical portion of the canaliculus, (2) a middle body or waist portion of smaller diameter around which the punctal sphincter ring tightens, and (3) a larger smooth head portion that sits on top of the punctal opening. The configuration of the plug and its relationship to the punctum and canaliculus prevents both the plug from being inadvertently extruded outward or from passing down into the canaliculus. In inserting the plug, the punctal opening and canaliculus are first dilated to about three times normal size with an awl-like dilator tool and the plug inserted using either a conventional forceps or alternatively a special rod-like inserter tool which releasably grips the head of the plug. The plug is firmly seated and retained in the punctal opening by the punctal sphincter ring and distended canaliculus, but yet can readily be pulled out when desired by grasping its head portion with forceps.

In addition to treating chronic dry eye condition, other potential therapeutically beneficial uses for the punctal plug technique disclosed herein include situations involving the long-time contact lens wearer with developing dry eye where preserving the tear fluid may allow the patient to wear his lenses with higher comfort and better vision for a further extended period of time. Also, in situations involving infection, inflammation or other ocular diseases, the punctum plug can serve as an effective vehicle for dispensing ophthalmic medication on a sustained release basis by impregnating the plug, or a cellular member attached thereto and resting in the lacrimal lake, with medication which is slowly leached out by the lacrimal fluids. Additionally, in glaucoma therapy where the eye tissue is treated with phospholine iodide or other topical therapy, the punctum plug would prevent drainage and thus systemic absorption of the drug, thus enhancing its therapeutic safety. Similarly, in situations where there is long-term lavaging of the eye, such as following chemical injury or in the treating of corneal ulcers, the punctal plug would prevent lavaging fluid and other medication from entering the nose and subsequent systemic absorption. Correlatively, by reason of the blockage of the punctum provided by the plug, topical medications applied to the eye are retained in contact therewith for greater periods of time; thus increased ocular absorption of such medication would likely occur with resultant increased efficacy.

It is therefore a principal objective of the present invention to provide a new and improved method for treating keratoconjunctivitis sicca and certain ophthalmic ailments by reversibly plugging the punctal opening of the eye.

It is a further principal objective of the present invention to provide a new and improved form of plug designed for insertion into and blocking off of the punctal opening of the eye for preventing the drainage therethrough of lacrimal fluid, but which is readily removable therefrom when desired.

It is yet a further principal objective of the present invention to provide a method for treating an infectious, inflamed or otherwise diseased eye by utilizing a punctum plug of the type described as a vehicle for storing and delivering ophthalmic medication to the eye on a sustained release basis.

It is a still further objective of the present invention to provide a method and means for removably inserting a plug into the punctal opening for completely blocking same.

It is a principal feature and advantage of the present invention to provide a punctal plug of strong, tissue-tolerable, sterilizable material which is designed to be firmly seated and held in the punctal opening by the punctal sphincter ring and associated canaliculus so that it will not inadvertently and undesirably be either ejected from the punctal opening or passed downward through the canaliculus.

The foregoing and other objectives, features and advantages of the present invention will be more readily understood upon consideration of the following detailed description of the invention, taken in conjunction with the accompanying drawings.

DETAILED DESCRIPTION OF THE INVENTION

Figure 1:
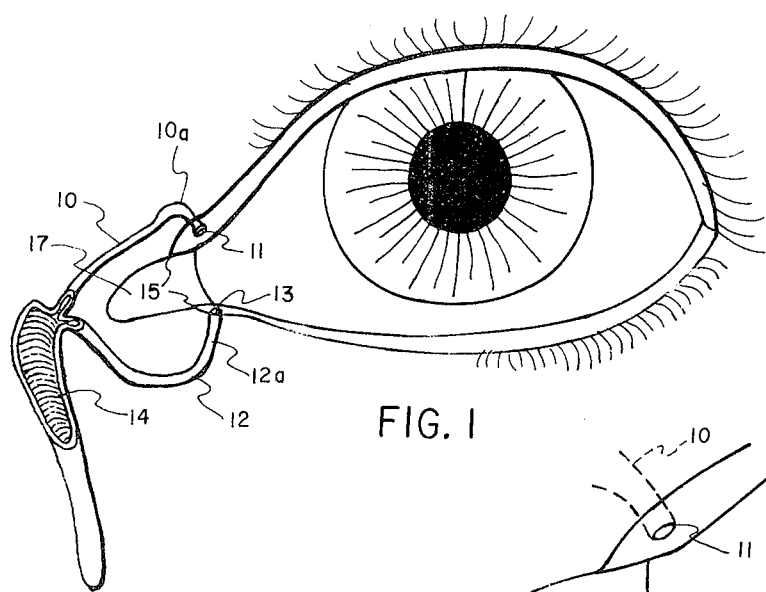
FIG. 1 is a representation of the anatomy of the human eye and associated lacrimal excretory system.

Referring to FIG. 1, there is shown a representation of the human eye anatomy and the associated lacrimal excretory system. For purposes of the present discussion it will be sufficient to focus on the latter which consists of the upper and lower lacrimal ducts 10 and 12, better known as the canaliculae, and the tear or lacrimal sac 14. The upper and lower canaliculae 10, 12 each terminate in respective small punctal apertures 11 and 13 situated on a slight elevation at the medial end of the lid margin at the junction 15 of the ciliary and lacrimal portions about 6 mm from the medial canthus 17. The punctal apertures are round or slightly ovoid openings approximately 0.3 mm in size and surrounded by a fairly dense, relatively avascular connective ring of tissue about 1 mm in depth. Each of the punctal openings 11, 13 leads into a vertical portion 10a, 12a of the respective canaliculus, which is about 2.5 to 3.5 mm in length, before turning horizontally for about 8 mm to join its other canaliculus at the entrance of a lacrimal sac 14. The canaliculae 10, 12 are tubular about 0.5 mm in diameter and lined by stratified squamous epithelium surrounded by elastic tissue which permits the canaliculus to be readily dilated to three times normal size as occurs in the punctum plug insertion technique hereinafter described.

Figure 2A:
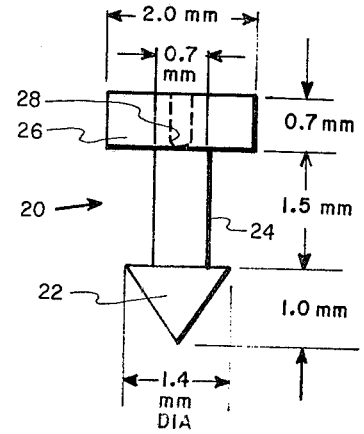
FIG. 2A is a plan view, with representative dimensions, of one embodiment of a punctal plug in accordance with the present invention.
Figure 2B:
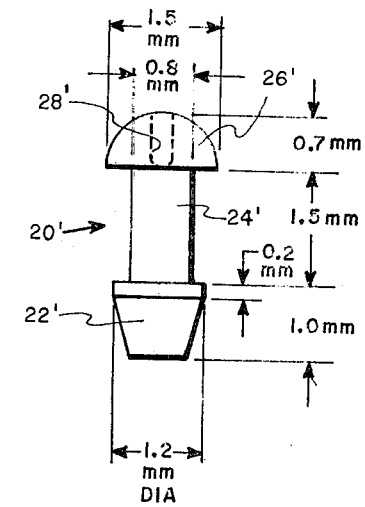
FIG. 2B is a plan view, with representative dimensions, of a second embodiment of a punctal plug.

As previously recited, in the treatment of keratoconjunctivitis sicca and other ophthalmic ailments where it is desired to prevent or decrease the drainage of lacrimal fluid and/or medication from the eye, the punctal aperture in either or both of the upper and lower lids are to be blocked by a removable plug member 20, two respective embodiments of which are shown in FIGS. 2A and 2B. Referring initially to the embodiment of FIG. 2A, the punctum plug 20 has an axial length of approximately 3.2 mm and consists of three portions; a projecting tip or barb portion 22, a middle neck or waist portion 24 of somewhat smaller diameter than the tip, and a smooth disc-like head portion 26 of relatively larger diameter. The plug embodiment 20' of FIG. 2B is of generally similar dimensions to the first-described embodiment with a somewhat blunted tip or barb portion 22', a cylindrical middle portion 24' of substantially the same dimension, and a dome-shaped head portion 26' of somewhat smaller diameter than its counterpart in the embodiment of FIG. 2A. The head portion 26, 26' of both embodiments may be provided, if desired as an alternative to grasping it with forceps, with a central bore opening 28, 28' adapted to receive the projecting tip of an inserter tool to provide a releasable grip on the plug as it is manipulated for insertion, as hereinafter described.

Both of the embodiments of FIGS. 2A and 2B have been successfully utilized in limited clinical testing of the punctum plugs in accordance with the techniques of the present invention. Materials found to be suitable for the composition of the punctum plug members 20 and 20' include polytetrafluoroethylene (Teflon) and hydroxyethylmethacrylate (HEMA) which is a hydrophilic polymer presently used in the manufacture of soft contact lenses. In clinical experiments plugs of HEMA hydrophilic polymer material displayed very excellent patient and tissue acceptance. In the dry state its firmness helped to ease the process of insertion and the plug became almost immediately soft and flexible as the drops of lacrimal fluid moistened it. In addition, its approximate 28% swell rate when moistened appeared to improve the closure of the punctal aperture more effectively. However, the tensile strength of the HEMA hydrophilic polymer material was somewhat less than desired and the plug was found to be subject to breakage when manipulated by a patient's finger. Plugs of Teflon polytetrafluoroethylene polymer material also displayed excellent tissue tolerance and very good patient acceptance, and were less susceptible to accidental breakage. In addition it is believed that silicon, stainless steel, aluminum and other metal and plastic materials which possess the necessary characteristics of tissue-inertness, high tensile strength to resist breakage, and ready sterilization such as by boiling in the case of the HEMA hydrophilic polymer, or by soaking in alcohol or similar sterilizing solution as in the case of Teflon, would also prove suitable as punctum plug materials.

Figures 3, 3A:
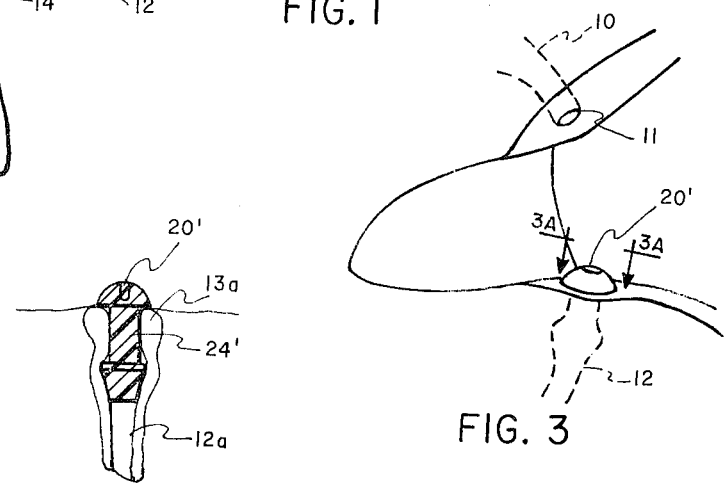
FIG. 3 is an enlarged view of a detail of the eye anatomy showing the punctal plug embodiment of FIG. 2B in place in the lower punctal opening.
FIG. 3A is a sectional view taken along line 3A—3A in FIG. 3.

The projecting tip or barb portion 22, 22' of the respective embodiments of the punctum plug is designed with either a tapered 22a or semi-tapered tip 22a' for further dilation and ease of insertion into the punctal opening. The tip portion 22, 22' is flared back to a somewhat larger base 22b, 22b', typically 1.2–1.4 mm in diameter, and then narrows down to a waist or neck portion 24, 24' of a somewhat smaller diameter, typically 0.7–0.8 mm. The distended vertical canaliculus 12a and the punctal sphincter ring 13a (FIG. 3A) tightens upon the respective tip and waist portions of the plug to firmly secure it from accidental extrusion. The head portion 26, 26' of the respective plug embodiments is sufficiently large, approximately 1.5–2.0 mm in diameter, as it rests on the punctal opening so as to prevent the plug from passing down into the canaliculus. The plug head is very smooth and of disc or dome shape which allows it to rest in the lacrimal lake and against conjunctivae and cornea with very little resultant irritation.

In certain embodiments of the invention the plugs 20, 20', particularly the head portion 28, 28', may be of medication-impregnable porous material such as HEMA hydrophilic polymer, or may be otherwise adapted as with capillaries or the like, to store and slowly dispense ophthalmic drugs to the eye as they are leached out by the lacrimal fluids.

Figure 4:
FIG. 4 is a plan view of a dilator tool for use in enlarging the punctum and associated canaliculus prior to receiving the punctal plug.

An exemplary technique for inserting the plug into the punctal aperture and associated canaliculus will now be set forth. The affected eye is first anesthetized with a topical anesthetic such as Properacaine, then a shortened cotton-tipped applicator is soaked in the same or similar topical anesthetic and put into the medial canthal area at the juncture of the upper and lower lid for 5 to 10 minutes. Next a punctum dilator 30, which as shown in FIG. 4 is in the form of an elongated rod of Teflon polytetrafluorethylene material terminating in a tapered awl-like flexible tip portion 32, is carefully used to slowly dilate the punctum and associated vertical canaliculus to about 2½ to 3 times its normal size, or about 1.2 mm, taking care to avoid breaking of the punctal connective tissue ring which, if it occurs, would produce until healed a looser, sloppier fit of the plug and possible accidental extrusion thereof.

Figure 5:
FIG. 5 is a plan view of an inserter tool for grasping, manipulating and inserting the plug into the punctal opening.
Figure 5A:
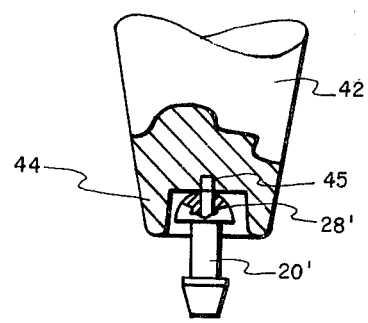
FIG. 5A is an enlarged view showing the detail of the head portion of the dilator tool of FIG. 5 grasping the punctum plug embodiment of FIG. 2B prior to insertion.

The plug itself is placed in the punctal opening with conventional forceps or with the aid of a special inserter tool 40 which, as shown in FIGS. 5 and 5A, is in the form of a pencil-like rod terminating in a blunted head 42 provided with a recessed central portion 44 of slightly larger diameter and deeper than the head portion 28, 28' of the respective punctum plugs 20, 20'. To temporarily engage the plug by its head portion, a thin finger member 45 projects outwardly from the center of the recess and is adapted to mate with a corresponding bore 28, 28' in the head of the plug. The friction fit is sufficiently tight between the projecting finger 45 and the mating bore hole 28, 28' that the plug is securely held by the inserter tool 40 as it is manipulated into the punctal aperture. As previously mentioned, the tip or barb portion 22, 22' of the plug is pointed, or at least partially so, to encourage some further dilation of the punctum and the canaliculus as the plug is inserted therein.

The plug is advanced into the depth of the canaliculus by manipulation of the inserter tool until the head portion 26, 26' is seated on the punctal opening. Thereupon, a simple shearing or wobbling motion of the inserter tool springs the projecting finger 45 from the plug head, permitting disengagement and removal of the tool leaving the punctum plug inserted in place. Following insertion the patient will usually experience some transient discomfort which can be relieved by aspirin or similar analgesic.

When it is desired to remove the plug, the head portion 26, 26' of the plug, or the neck 24, 24' just under the head, may be grasped with forceps and the plug withdrawn from the punctal opening. If necessary, topical anesthetic can be applied for the removal technique in which case, as an alternative or in addition to the use of forceps, the plug may be squeezed out of the punctal opening by pressure applied to the horizontal portion of the canaliculus, accompanied by movement toward the punctal opening.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A removable rod-like plug for blocking lacrimal fluid flow through the punctum and associated canaliculus of the human eye comprising: a projecting tip portion having a maximum cross-sectional dimension in the range of about 1.0 to 1.4 mm which is sufficient to occlude the canaliculus when inserted therein, a middle neck portion of smaller cross-section than the largest part of said tip portion with a maximum dimension in the range of about 0.6 to 0.8 mm and adapted to be tightened upon by the punctum sphincter ring, said tip and neck portions cooperating with said canaliculus and punctum sphincter ring respectively to prevent accidental extrusion of said plug, and a head portion of larger cross-section than said neck portion and adapted to rest on the surface of the punctal aperture and prevent said plug from passing down into the canaliculus, with the overall length of said plug comprised of said tip, neck and head portions being not less than about 3.2 mm.

2. The punctum plug of claim 1 wherein said respective tip, neck and head portions thereof are each of circular cross-section and said tip portion is of generally forwardly tapered configuration for dilating the canaliculus when inserted therein.

3. The punctum plug of claim 1 wherein said plug is unitary and comprised of tissue-tolerable, readily sterilizable, inert material selected from the group consisting of polytetrafluorethylene and hydroxyethylmethacrylate hydrophilic polymer.

4. The punctum plug of claim 1 wherein said head portion thereof is comprised of a medicament-impregnable porous material for storing and slowly dispensing an ophthalmic fluid medication to the eye while said plug is inserted into the punctal opening.

5. A means for removably blocking lacrimal fluid flow through the punctum and associated canaliculus of the human eye comprising a plug-shaped body portion of cross-section sufficient to at least substantially occlude the punctal aperture and associated vertical canaliculus when inserted therein, and an enlarged head portion so sized relative to said aperture that when said plug is inserted into the punctum and canaliculus it will rest upon the surface of the punctal aperture, said head portion being of a porous tissue-tolerable polymer material and containing a reservoir therein of an ophthalmic fluid medication which is slowly dispensed to the surface of the eye by the leaching action of the lacrimal fluids thereon.

6. The punctum plug of claim 5 wherein said head portion is of material selected from the group consisting of polytetrafluorethylene and hydroxyethylmethacrylate hydrophilic polymer.

7. A method for treating and alleviating keratoconjunctivitis sicca (dry eye) resulting from insufficient production or excessive drainage of lacrimal fluid comprising the steps of:

a. dilating the punctum and associated vertical canaliculus to about two and one-half times or greater normal size;
b. thereafter inserting a removable rod-like plug into the punctum and associated vertical canaliculus to occlude the punctal opening and prevent the passage of lacrimal fluid therethrough, said plug being sized and configured so as to be firmly retained in said punctal opening against accidental extrusion by the frictional engagement therewith of the distended canaliculus and punctum sphincter ring; and
c. maintaining the plug in place for a sustained and effective period of time to treat said condition.

8. The method of claim 7 further including the step of dispensing an ophthalmic fluid medication on a sustained release basis to the eye from a reservoir of such medication stored in said plug and dispensed through openings therein.

9. A method for treating ophthalmic ailments requiring the topical application of a fluid medication to an afflicted eye over repeated or sustained periods of time, said method comprising the steps of:
a. impregnating with said medication at least a portion of a plug element of size and configuration adapted to be removably fitted into the punctum and associated vertical canaliculus of an afflicted eye; and
b. inserting said medicament-impregnated plug into said punctum and associated vertical canaliculus to be retained therein for a sufficient period of time to dispense an effective amount of said medication to said afflicted eye.

10. The method of claim 9 wherein, prior to said insertion step (b), said punctum and associated vertical canaliculus are dilated to about 2½ times or greater their normal size.

* * * * *

UNITED STATES PATENT AND TRADEMARK OFFICE
CERTIFICATE OF CORRECTION

PATENT NO. : 3,949,750
DATED : April 13, 1976
INVENTOR(S) : Jerre M. Freeman

It is certified that error appears in the above-identified patent and that said Letters Patent are hereby corrected as shown below:

Title                Change "Aliments" to --Ailments--.

Col. 1    Line 26    Change "Sjogren's" to --Sjögren's--.

Signed and Sealed this

Twenty-seventh Day of July 1976

[SEAL]

Attest:

RUTH C. MASON
*Attesting Officer*

C. MARSHALL DANN
*Commissioner of Patents and Trademarks*